United States Patent [19]

Vale, Jr. et al.

[11] 4,386,074

[45] * May 31, 1983

[54] LRF ANTAGONISTS

[75] Inventors: Wylie W. Vale, Jr.; Jean E. F. Rivier, both of La Jolla, Calif.

[73] Assignee: The Salk Institute for Biological Studies, San Diego, Calif.

[*] Notice: The portion of the term of this patent subsequent to Sep. 29, 1998, has been disclaimed.

[21] Appl. No.: 287,189

[22] Filed: Jul. 27, 1981

Related U.S. Application Data

[63] Continuation-in-part of Ser. No. 182,594, Aug. 29, 1980, abandoned.

[51] Int. Cl.³ .................. A61K 37/00; C07C 103/52
[52] U.S. Cl. ........................... 424/177; 260/112.5 LH
[58] Field of Search ............... 260/112.5 LH; 424/177

[56] References Cited

U.S. PATENT DOCUMENTS 4,215,038  7/1980  Rivier et al. .............. 260/112.5 LH

OTHER PUBLICATIONS

"Peptides", Structure and Biological Function, Coy et al., Article, pp. 775–779.
Journal of Medicinal Chemistry, 1977, vol. 20, No. 4, pp. 495–500.
Int. J. Peptide Protein Res., vol. 10, 1977, Felix et al., pp. 299–310.
Chem. Abstr. 91, 1979, p. 33213d.
C. W. Beattie, J. of Med. Chem. 18, No. 12, 1975, 1247–1250.

Primary Examiner—Delbert R. Phillips
Attorney, Agent, or Firm—Fitch, Even, Tabin, Flannery & Welsh

[57] ABSTRACT

Peptides which inhibit the secretion of gonadotropins by the pituitary gland and inhibit the release of steroids by the gonads. Administration of an effective amount prevents ovulation of female mammalian eggs and/or the release of steroids by the gonads. The peptides have the structure:

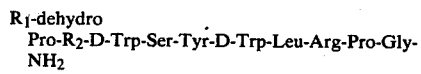

$R_1$-dehydro Pro-$R_2$-D-Trp-Ser-Tyr-D-Trp-Leu-Arg-Pro-Gly-$NH_2$ wherein $R_1$ is selected from the group consisting of hydrogen, formyl, acetyl, acrylyl, benzoyl and allyl; $R_2$ is selected from the group consisting dichloro-D-Phe, $C^\alpha Me4Cl$-D-Phe, $(CH_3)_5$-D-Phe, $CF_3$-D-Phe, F-D-Phe, difluoro-D-Phe, AcNH-D-Phe, $NO_2$-D-Phe, dinitro-D-Phe, Br-D-Phe, dibromo-D-Phe, $CH_3S$-D-Phe, $OCH_3$-D-Phe and $CH_3$-D-Phe, wherein any D-isomer amino acid can be substituted for D-Trp in the 6-position, and wherein $N^\alpha MeLeu$ may be substituted for Leu.

20 Claims, No Drawings

LRF ANTAGONISTS

This invention described herein was made in the course of work under a grant or award from the Department of Health and Human Services.

This application is a continuation-in-part of our earlier application Ser. No. 182,594, filed Aug. 29, 1980, now abandoned.

The present invention relates to peptides which inhibit the release of gonadotropins by the pituitary gland in mammalians, including humans, and to methods of preventing ovulation and/or inhibiting the release of steroids. More particularly, the present invention is directed to peptides which inhibit gonadal function and the release of the steroidal hormones, progesterone and testosterone.

The pituitary gland is attached by a stalk to the region in the base of the brain known as the hypothalamus. The pituitary gland has two lobes, the anterior and the posterior lobes. The posterior lobe of the pituitary gland stores and passes onto the general circulation two hormones manufactured in the hypothalamus, these being vasopressin and oxytocin. The anterior lobe of the pituitary gland secretes a number of hormones, which are complex protein or glycoprotein molecules that travel through the bloodstream to various organs and which, in turn, stimulate the secretion into the blood stream of other hormones from the peripheral organs. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH. The hypothalamic hormone which acts as a releasing factor for LH is referred to herein as LRF although it has also been referred to as LH-RH and as GnRH. LRF has been isolated and characterized as a decapeptide having the following structure:
p-Glu-His-Trp-Ser-Tyr-Gly-Leu-Arg-Pro-Gly-NH$_2$ Peptides are compounds which contain two or more amino acids in which the carboxyl group of one acid is linked to the amino group of the other acid. The formula for LRF, as represented above, is in accordance with conventional representation of peptides where the amino group appears to the left and the carboxyl group to the right. The position of the amino acid residue is identified by numbering the amino acid residues from left to right. In the case of LRF, the hydroxyl portion of the carboxyl group of glycine has been replaced with an amino group (NH$_2$). The abbreviations for the individual amino acid residues above are conventional and are based on the trivial name of the amino acid: where p-Glu is pyroglutamic acid, His is histidine, Trp is tryptophan, Ser is serine, Tyr is tyrosine, Gly is glycine, Leu is leucine, Arg is arginine and Pro is proline. Except for glycine, amino acids of the peptides of the invention are of the L-configuration unless noted otherwise. Acetyl is abbreviated as Ac, and acrylyl is abbreviated as Acr.

It is known that the substitution of D-amino acids for Gly in the 6-position of the LRF decapeptide provides a peptide material having from about 1 to 35 times greater potency than does LRF to effect the release of LH and other gonadotropins by the pituitary gland of mammalians. The releasing effect is obtained when the LRF analog is introduced into the bloodstream of a mammalian.

It is also known that substitution of various amino acids for His (or the deletion of His) at the 2-position of the LRF decapeptide produces analogs having an inhibitory effect on the release of LH and other gonadotropins by the pituitary gland of mammalians. In particular, varying degrees of inhibition of the release of LH are obtained when His is deleted (des His) or replaced by D-Ala, D-Phe or Gly. The inhibitory effect of such peptides modified at the 2-position can be further enhanced when a D-amino acid is substituted for Gly in the 6-position of the decapeptides. For example, the peptide: pGlu-Trp-Ser-Tyr-D-Ala-Leu-Arg-Pro-Gly-NH$_2$ is 4 times more potent as an inhibitor for the release of gonadotropins than is the same peptide where Gly is present in the 6-position rather than D-Ala.

Some female mammalians who have no ovulatory cycle and who show no pituitary or ovarian defect begin to secrete normal amounts of the gonadotropins LH and FSH after the appropriate administration of LRF. Thus, the administration of LRF is considered suitable for the treatment of those cases of infertility where a functional defect resides in the hypothalamus.

There are also reasons for desiring to prevent ovulation in female mammalians, and the administration of LRF analogs that are antagonistic to the normal function of LRF have been used to prevent ovulation. For this reason, analogs of LRF which are antagonistic to LRF are being investigated for their potential use as a contraceptive or for regulating conception periods. It is desired to provide peptides which are strongly antagonistic to endogenous LRF and which prevent secretion of LH and the release of steroids by the gonads of mammals.

The present invention provides peptides which inhibit the release of gonadotropins in mammalians, including humans, and also provides methods for inhibiting the release of steroids by the gonads of male and female mammalians. The improved LRF analogs are antagonistic to LRF and have an inhibitory effect on the reproduction processes of mammalians. These analogs may be used to inhibit the production of gonadotropins and sex hormones under various circumstances including precocious puberty; hormone dependent neoplasia, dysmenorrhea and endometreosis.

Generally, in accordance with the present invention, peptides have been synthesized which strongly inhibit the secretion of gonadotropins by the pituitary gland of mammalians, including humans, and/or inhibit the release of steroids by the gonads. These peptides are analogs of LRF wherein there are substitutions in the 1- and 2-positions, and D-Trp may be present in the 3- and 6-positions. Other D-isomer amino acids may be used in the 6-position, but preferably an aromatic D-isomer amino acid, such as D-Trp or (imBzl) D-His, is used. The 1-position contains dehydro-Pro or a modification thereof wherein its alpha amino group contains formyl, acetyl, acrylyl, benzoyl or allyl. By dehydro Pro is meant 3,4 dehydroProline, C$_5$H$_7$O$_2$N, and when R$_1$ is acyl or alkyl radical, it is attached to the nitrogen. Modified D-Phe is present in the 2-position and provides increased antagonistic activity as a result of the specific modifications present in the benzene ring. Single substitutions are made for hydrogen, preferably in the 4-position, and double substitutions are made preferably in the 2,4 or the 3,4 positions. The substitutions are selected from dichloro, methyl, fluoro, difluoro, trifluoromethyl, methoxy, bromo, dibromo, nitro, dinitro acetylamino, pentamethyl and methyl mercapto. In addition, the methyl substitution on the α-carbon plus the para-chloro substitution can be used.

Because these peptides are highly potent to inhibit release of LH, they are often referred to as LRF antagonists. The peptides inhibit ovulation of female mammals when administered at very low levels at proestrous and are also effective to cause resorption of fertilized eggs if administered shortly after conception.

More specifically, the peptides of the precent invention are represented by the following formula:
$R_1$-dehydro Pro-$R_2$-D-Trp-Ser-Tyr-D-Trp-Leu-Arg-Pro-Gly-$NH_2$
wherein $R_1$ is selected from the group consisting of hydrogen, formyl, acetyl, acrylyl, benzoyl and allyl; $R_2$ is selected from the group consisting of dichloro-D-Phe, F-D-Phe, difluoro-D-Phe, $CF_3$-D-Phe, AcNH-D-Phe, dinitro-D-Phe, $NO_2$-D-Phe, dibromo-D-Phe, Br-D-Phe, $C^\alpha$ Me4Cl-D-Phe, $(CH_3)_5$-D-Phe, $CH_3S$-D-Phe, $OCH_3$-D-Phe and $CH_3$-D-Phe; wherein any D-isomer amino acid can be substituted for D-Trp in the 6-position; and wherein $N^\alpha$MeLeu may be substituted for Leu.

The peptides of the present invention can be synthesized by a solid phase technique using a chloromethylated resin, a methylbenzhydrylamine resin (MBHA) or a benzhydrylamine (BHA) resin. The synthesis is conducted in a manner to stepwise add the amino acids in the chain in the manner set forth in detail in the U.S. Pat. No. 4,211,693, the disclosure of which is incorporated herein by reference. Side-chain protecting groups, as are well known in the art, are added to Ser, Tyr, Arg and His before these amino acids are coupled to the chain being built up upon the resin.

Such a method provides the fully protected intermediate peptidoresin. The fully protected peptide can be cleaved from the chloromethylated resin support by ammonolysis, as is well known in the art, to yield the fully protected amide intermediate. The intermediates of the invention may be represented as:
$X^1$-dehydro Pro-$R_2$-D-Trp-Ser($X^2$)-Tyr($X^3$)-D-Trp-Leu-Arg($X^4$)-Pro-Gly-$X^5$
wherein: $X^1$ is an α-amino protecting group of the type known to be useful in the art in the stepwise synthesis of polypeptides and when $R_1$ in the desired peptide composition is a particular acyl or alkyl group, that group may be used as the protecting group. Among the classes of α-amino protecting groups covered by $X^1$ are (1) acyl-type protecting groups, such as formyl, trifluoroacetyl, phthalyl, Tos, benzoyl, benzensulfonyl, nitrophenylsulfenyl, tritylsulfenyl, o-nitrophenoxyacetyl, acrylyl, chloroacetyl, acetyl and γ-chlorobutyryl; (2) aromatic urethan-type protecting groups, e.g., benzyloxycarbonyl and substituted benzyloxycarbonyl, such as p-chloro-benzyloxycarbonyl, p-nitrobenzyloxycarbonyl, p-bromobenzyl-oxycarbonyl and p-methoxybenzyloxycarbonyl; (3) aliphatic urethan protecting groups, such as terbutyloxycarbonyl (Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl, triphenylmethyl(trityl) and benzyl; (7) trialkylsilane groups, such as trimethylsilane. The preferred α-amino protecting group is Boc when $R_1$ is hydrogen.

$X^2$ is a protecting group for the alcoholic hydroxyl group of Ser and is selected from the group consisting of acetyl, benzoyl, tetrahydropyranyl, tert-butyl, trityl, benzyl and 2,6-dichlorobenzyl. Benzyl is preferred.

$X^3$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl.

$X^4$ is a protecting group for the nitrogen atoms of Arg and is selected from the group consisting of nitro, Tos, benzyloxycarbonyl, adamantyloxycarbonyl, and Boc; alternatively $X^4$ may be hydrogen, which means there are no protecting groups on the side chain nitrogen atoms of arginine.

$X^5$ is selected from or Gly-O-$CH_2$-[resin support] or Gly-NH-[resin support].

The criterion for selecting side chain protecting groups for $X^2$-$X^4$ is that the protecting group must be stable to the reagent under the reaction conditions selected for removing the α-amino protecting group at each step of the synthesis. The protecting group must not be split off under coupling conditions, and the protecting group must be removable upon completion of the synthesis of the desired amino acid sequence under reaction conditions that will not alter the peptide chain.

When the $X^5$ group is Gly-O-$CH_2$-[resin support], the ester moiety of one of the many functional groups of the polystyrene resin support is being represented. When the $X^5$ group is Gly-NH-[resin support], an amide bond connects Gly to BHA resin or to a methyl BHA resin.

When $R_1$ is acetyl, formyl, acrylyl, benzoyl, or allyl, it may be employed as the $X^1$ protecting group for the α-amino group of proline in which case it can be added to proline before it is coupled to the peptide chain. Alternatively, a reaction may be carried out with the peptide on the resin, e.g. reacting with acetic acid in the presence of dicyclohexyl carbodiimide (DCC) or with acetic anhydride.

Deprotection of the peptides as well as cleavage of the peptide from the benzhydrylamine resin takes place at 0° C. with hydrofluoric acid (HF). Anisole is added to the peptide prior to treatment with HF. After the removal of HF, under vacuum, the cleaved, deprotected peptide is treated with ether, decanted, taken in dilute acetic acid and lyophilized.

Purification of the peptide is effected by ion exchange chromotography on a CMC column, followed by partition chromotography using the elution system: n-butanol; 0.1 N acetic acid (1:1 volume ratio) on a column packed with Sephadex G 25. The peptides of the invention are effective at levels of less than 200 micrograms per kilogram of body weight, when administered at about noon on the day of proestrous, to prevent ovulation in female rats. For prolonged suppression of ovulation, it may be necessary to use dosage levels in the range of from about 0.1 to about 5 milligrams per kilogram of body weight. These antagonists are also effective as contraceptives when administered to male mammals on a regular basis.

Since those compounds will reduce testosterone levels (an undesired consequence in the normal, sexually active male), it may be reasonable to administer replacement dosages of testosterone along with the LRF antagonist.

The following examples further illustrate various features of the invention but are intended to in no way limit the scope of the invention which is defined in the appended claims.

EXAMPLE

The following peptides having the formula $R_1$-dehydro Pro-$R_2$-D-Trp-Ser-Tyr-D-Trp-Leu-Arg-Pro-Gly-$NH_2$ are prepared by the solid phase procedure referred to above.

TABLE I

| PEPTIDE | $R_1$ | $R_2$ |
|---|---|---|
| 1 | Ac | 3,4 $Cl_2$—D-Phe |
| 2 | " | 4 $CF_3$—D-Phe |
| 3 | " | 4 F—D-Phe |
| 4 | " | 4 AcNH—D-Phe |
| 5 | " | 4 $NO_2$—D-Phe |
| 6 | " | 4 Br—D-Phe |
| 7 | " | 4 $CH_3$S—D-Phe |
| 8 | " | 4 $OCH_3$—D-Phe |
| 9 | " | 4 $CH_3$—D-Phe |
| 10 | " | 2,4 $Cl_2$—D-Phe |
| 11 | Acr | 3,4 $Cl_2$—D-Phe |
| 12 | Ac | 4 $OCH_3$—D-Phe($N^\alpha$MeLeu$^7$) |
| 13 | " | 4 $CH_3$—D-Phe($N^\alpha$MeLeu$^7$) |
| 14 | " | 3,4 $Cl_2$—D-Phe($N^\alpha$MeLeu$^7$) |
| 15 | " | $(CH_3)_5$—D-Phe |
| 16 | " | $C^\alpha$MeCl—D-Phe |
| 17 | " | 3 F—D-Phe |

For purposes of an example, a representative solid phase synthesis of Peptide No. 1 above, which is referred to as [Ac-dehydro Pro$^1$, 3,4 $Cl_2$-D-Phe$^2$, D-Trp$^{3,6}$]-LRF is set forth hereinafter. This peptide has the following formula:

Ac-dehydro Pro-3,4 $Cl_2$-D-Phe-D-Trp-Ser-Tyr-D-Trp-Leu-Arg-Pro-Gly-$NH_2$

A BHA resin is used, and Boc-protected Gly is coupled to the resin over a 2-hour period in $CH_2Cl_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 10 |
| 5 | $CH_2Cl_2$ wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular amino acid, (1 time) plus DCC (10 mmoles) in $CH_2Cl_2$ | 30–300 |
| 10 | MeOH wash-40 ml. (2 times) | 3 |
| 11 | TEA 12.5 percent in $CH_2Cl_2$-70 ml. (1 time) | 3 |
| 12 | MeOH wash-30 ml. (2 times) | 3 |
| 13 | $CH_2Cl_2$ wash-80 ml. (2 times) | 3 |

After step 13, an aliquot is taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. $N^\alpha$Boc protection is used for each of the remaining amino acids throughout the synthesis. The side chain of Arg is protected with Tos. OBzl is used as a side chain protecting group for the hydroxyl group of Ser, and 2-6 dichlorobenzyl is used as the side chain protecting group for the hydroxyl group of Tyr. N-acetyl-dehydro Pro is introduced as the final amino acid. Boc-Arg(Tos) and Boc-D-Trp, which have low solubility in $CH_2Cl_2$, are coupled using DMF.

The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3 M $NH_4OAc$ in 50/50 methanol/water) followed by partition chromatography in a gel filtration column using the elution system: n-Butanol; 0.1 N Acetic acid (1:1-volume ratio).

The peptides set forth in the foregoing table are assayed in vitro and in vivo. The in vitro test is made using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in LRF: experimental dishes receive a measure 3 nanomolar in LRF plus a measure having a concentration of test peptide ranging from 0.01 to 3 nanomolar. The amount of LH secreted in the samples treated only with LRF is compared with that secreted by the samples treated with the peptide plus LRF. Results are calculated and expressed in Table II (In Vitro column) as the molar concentration ratio of test peptide to LRF (antagonist/LRF) required to reduce the amount of LH released by 3 nanomolar LRF to 50 percent of the control value ($ICR_{50}$).

The peptides described hereinabove are used to determine effectiveness to prevent ovulation in female rats. In this test, a specified number of mature female Sprague-Dawley rats, each having a body weight from 225 to 250 grams, are injected with either 5 or 10 micrograms of peptide in corn oil at about noon on the day of proestrous. Proestrous is the afternoon before estrous (ovulation). A separate female rat group is used as a control to which the peptide is not administered. Each of the control rat females has ovulation at estrous. As indicated in the In Vivo column, the peptides are significantly effective to prevent ovulation of female rats at a very low dosage, and all of the peptide compositions are considered to be totally effective at a dose of one milligram.

TABLE II

| Peptide | In Vitro $ICR_{50}$ | In Vivo (10μg) Rats Ovulating | In Vivo (5μg) Rats Ovulating |
|---|---|---|---|
| 1 | 0.039 | | 1/10 |

TABLE II-continued

| Peptide | In Vitro ICR$_{50}$ | In Vivo (10μg) Rats Ovulating | In Vivo (5μg) Rats Ovulating |
| --- | --- | --- | --- |
| 2 | 0.070 | | 7/9 |
| 3 | 0.021 | | 0/10 |
| 4 | 0.500 | 9/10 | |
| 5 | 0.011 | | 2/10 |
| 6 | 0.010 | | 5/7 |
| 7 | 0.030 | | 7/10 |
| 8 | 0.125 | 3/10 | |
| 9 | 0.044 | 1/7 | |
| 10 | 0.034 | | 4/7 |
| 11 | 0.048 | | |
| 12 | 0.29 | 5/10 | |
| 13 | 0.11 | 3/4 | |
| 14 | 0.05 | 1/3 | |
| 15 | 0.375 | 7/10 | |
| 16 | 0.045 | 2/10 | |
| 17 | | 5/7 | |

These peptides can be administered to mammals intravenously, subcutaneously, intramuscularly or orally to achieve fertility inhibition and/or control. Effective dosages will vary with the form of administration and the particular species of mammal being treated. An example of one typical dosage form is a physiological saline solution containing the peptide which solution is administered to provide a dose in the range of about 0.1 to 5 mg/kg of body weight. Oral administration of the peptide may be given in either solid form or liquid form.

Although the invention has been described with regard to its preferred embodiments, it should be understood that changes and modifications as would be obvious to one having the oridinary skill in this art may be made without departing from the scope of the invention which is set forth in the claims which are appended hereto. For example, other substitutions known in the art which do not significantly detract from the effectiveness of the peptides may be employed in the peptides of the invention.

What is claimed is:

1. A peptide or a nontoxic salt thereof, said peptide having the formula:

$R_1$-dehydro Pro-$R_2$-D-Trp-Ser-Tyr-D-Trp-Leu-Arg-Pro-Gly-NH$_2$ wherein $R_1$ is selected from the group consisting of hydrogen, formyl, acetyl, acrylyl, benzoyl and allyl; $R_2$ is selected from the group consisting of dichloro-D-Phe, CF$_3$-D-Phe, F-D-Phe, difluoro-D-Phe, AcNH-D-Phe, NO$_2$-D-Phe, dinitro-D-Phe, Br-D-Phe, dibromo-D-Phe, C$^\alpha$Me4Cl-D-Phe, (CH$_3$)$_5$-D-Phe, CH$_3$S-D-Phe, OCH$_3$-D-Phe and CH$_3$-D-Phe; wherein any D-isomer amino acid may be substituted for D-Trp and in the 6-position; and wherein N$^\alpha$MeLeu may be substituted for Leu.

2. A peptide in accordance with claim 1 wherein $R_1$ is acetyl and $R_2$ is dichloro-D-Phe.

3. A peptide in accordance with claim 1 wherein $R_1$ is acetyl and $R_2$ is 4 CF$_3$-D-Phe.

4. A peptide in accordance with claim 1 wherein $R_1$ is acetyl and $R_2$ is 4 AcNH-D-Phe.

5. A peptide in accordance with claim 1 wherein $R_1$ is acetyl and $R_2$ is 4 NO$_2$-D-Phe.

6. A peptide in accordance with claim 1 wherein $R_1$ is acetyl and $R_2$ is 4 Br-D-Phe.

7. A peptide in accordance with claim 1 wherein $R_1$ is acetyl and $R_2$ is 4 CH$_3$S-D-Phe.

8. A peptide in accordance with claim 1 wherein $R_1$ is acetyl and $R_2$ is 4 OCH$_3$-D-Phe.

9. A peptide in accordance with claim 1 wherein $R_1$ is acetyl and $R_2$ is 4 CH$_3$-D-Phe.

10. A peptide in accordance with claim 1 wherein $R_1$ is acetyl and $R_2$ is (CH$_3$)$_5$-D-Phe.

11. A peptide in accordance with claim 1 wherein $R_1$ is acetyl and $R_2$ is C$^\alpha$Me4Cl-D-Phe.

12. A peptide in accordance with claim 1 wherein $R_1$ is acrylyl.

13. A peptide in accordance with claim 1 wherein $R_1$ is acetyl and $R_2$ is 4-F-D-Phe.

14. A peptide in accordance with claim 1 wherein $R_1$ is acetyl.

15. A peptide in accordance with claim 14 wherein $R_2$ is 2,4 Cl$_2$-D-Phe.

16. A peptide in accordance with claim 14 wherein $R_2$ is 3,4 Cl$_2$-D-Phe.

17. A method for preventing ovulation of female mammalian eggs comprising administering an effective amount of a peptide, or a nontoxic salt thereof, to a female mammal, said peptide having the formula:

$R_1$-dehydro Pro-$R_2$-D-Trp-Ser-Tyr-D-Trp-Leu-Arg-Pro-Gly-NH$_2$ wherein $R_1$ is selected from the group consisting of hydrogen, formyl, acetyl, acrylyl, benzoyl and allyl; $R_2$ is selected from the group consisting of dichloro-D-Phe, CF$_3$-D-Phe, F-D-Phe, difluoro-D-Phe, AcNH-D-Phe, NO$_2$-D-Phe, dinitro-D-Phe, Br-D-Phe, dibromo-D-Phe, C$^\alpha$Me4Cl-D-Phe, (CH$_3$)$_5$-D-Phe, CH$_3$S-D-Phe, OCH$_3$-D-Phe and CH$_3$-D-Phe; wherein any D-isomer amino acid may be substituted for D-Trp in the 6-position; and wherein N$^\alpha$MeLeu may be substituted for Leu.

18. A method in accordance with claim 17 wherein $R_1$ is acetyl and $R_2$ is 4 F-D-Phe.

19. A method in accordance with claim 17 wherein $R_2$ is dichloro-D-Phe.

20. A method in accordance with claim 17 wherein $R_2$ is 4 NO$_2$-D-Phe.

* * * * *